United States Patent [19]

Lipson

[11] Patent Number: 5,000,168
[45] Date of Patent: Mar. 19, 1991

[54] PORTABLE MULTI-POSITIONAL HUMAN LIMB SUPPORTER

[76] Inventor: Walda B. Lipson, 131 Soundview Ave., White Plains, N.Y. 10606

[21] Appl. No.: 438,597

[22] Filed: Nov. 17, 1989

[51] Int. Cl.⁵ .............................................. A61F 5/10
[52] U.S. Cl. ...................................... 128/77; 128/88; 128/845; 128/87 R
[58] Field of Search ..................... 128/77, 80 R, 25 R, 128/845, 88, 99.1, 108.1, 87 R; 297/429

[56] References Cited

U.S. PATENT DOCUMENTS

| | | | |
|---|---|---|---|
| 2,978,713 | 4/1961 | Scalzitti et al. | 128/845 |
| 4,092,043 | 5/1978 | Wieland | 299/429 |
| 4,538,600 | 9/1985 | Hepburn | 128/77 X |
| 4,577,623 | 3/1986 | Pecheux | 128/25 R |
| 4,660,550 | 4/1987 | Bodine | 128/77 |
| 4,899,735 | 2/1990 | Townsend et al. | 128/25 R X |

Primary Examiner—Robert A. Hafer
Assistant Examiner—Kerry Owens
Attorney, Agent, or Firm—George A. Skoler

[57] ABSTRACT

The present invention is directed to a portable and multi-positional limb support which not only provides support for a patient's limb when the support is placed on a fixed surface but moreover, provides support for an arm even when that patient is stationary or ambulatory.

15 Claims, 6 Drawing Sheets

PORTABLE MULTI-POSITIONAL HUMAN LIMB SUPPORTER

FIELD OF THE INVENTION

This invention pertains to the field of human limb supports for use by invalids or convalescents to support an arm or leg while healing and is more particularly directed to a portable and multi-positional limb support which provides support (i) for either an arm or leg when the support is placed on a fixed surface and (ii) for an arm when the person is stationary or ambulatory.

BACKGROUND OF THE INVENTION

After undergoing surgery, suffering a stroke, or mending a broken bone, it is frequently necessary to position the body, particularly one or more of the limbs, in a manner which aids the healing process and, in many instances, makes the patient more comfortable. In many cases, elevating a limb aids the healing process. Elevation of a limb serves to avoid or decrease swelling or the accumulation of fluids (i.e. edemas) in the limb.

Devices exist which help support a limb in fixed positions. Certain of the devices utilize pulleys suspended from above the patient. Other devices are rested on a fixed surface such as a floor, the arm of a chair or a table top. For patients that are ambulatory and would require support of an arm in one or more different positions, such as an inclined position, while stationary, walking, or just moving about in a work activity, the choice of device is fairly limited. A typical fabric-type sling is usually utilized for such ambulatory support. In that case, the arm is essentially kept in one position—up against the body—and is not elevated since the sling is supported by the patient's shoulders and/or neck. Casted supports, which range from plaster to fabric or scrim reinforced plastic materials, are utilized in a manner that holds the limb in a fixed position relative to the body. Cast supports including an angle brace, may be used to prop up the limb to an elevated position, but this technique of elevating a limb does not offer comfort, convenience and, most significantly, the ability to conveniently accommodate the limb to a plurality of positions in the course of the healing process or while the patient is in a peripatetic mode.

Clearly, a need exists to provide a limb support which is multi-positional when the support is resting on a fixed surface, inclined, round or flat (of different heights)

used as an arm support when the patient is stationary or ambulatory.

SUMMARY OF THE INVENTION

This invention is directed to a limb support device capable of providing sufficient support to a limb so as to avoid gravitationally induced stress on the proximal joints to the limb, such as the shoulder/arm joint, and which is multi-positional when the support is resting on a fixed surface, inclined, round or flat (of different heights)

used as an arm support when the patient is stationary or ambulatory.

The limb supporter of the present invention is a remarkably adaptable device because it adjusts to any resting surface height, it adjusts to any resting surface contour, it accepts a wide range of height elevations over a wide range of posture positions thereby allowing its height to be adjusted to accommodate an almost limitless incremental array of correlations of heights and postures of the patient, it is an arm supporter while the patient is at rest or is ambulatory, with the same degree of adjustability, and it provides arm support over a range of patient activities, regardless of whether the patient engages in a variety of ambulatory activities or a combination of ambulatory and non-ambulatory activities (viz., sitting, walking, bending, etc.).

In addition, the limb support of the invention when used in the ambulatory support of an arm, distributes the weight of the arm to a part of the body that is most comfortable to the patient for carrying that weight. And this is possible regardless of the height the limb support positions the arm. In addition to height adjustment, the supporter of the present invention is also capable of being angularly positioned so as to accommodate any desired limb support angle. The utilitarian flexibility of the supporter of the invention is further demonstrated by its ability to provide multi-positional, stable limb support while resting on a fixed surface such as the patient's lap, on the arm of a chair or sofa, car seat, car seat armrest or on a flat surface such as a table, bed or the like. Most important to the patient is the ability of the limb supporter of the present invention to provide multi-positional stable support to an arm even when the patient is at rest or ambulatory in a variety of ways.

Specifically, the limb supporter of the present invention is provided with a base (bottom surface) having a frictional-engagement cushioning layer which is suitable for providing frictional engagement with the body of the patient yet produces no soreness to the patient. In this manner, the base of the limb supporter may be placed up against a portion of a patient's body capable of easily carrying the weight of the arm without inducing stress to the arm/shoulder joint, e.g., a patient's hip, such that the frictional-engagement cushioning layer touches and rest against that portion of the body and thereby is frictionally engaged by the body at that point. When the arm is positioned on the supporter, the weight of the arm on the supporter is correspondingly transferred to the frictional-engagement cushioning layer and relatively gently absorbed by that portion of the body. This enables the supporter to be substantially fixed in the placed position on the body with relatively minimum discomfiture to the patient. Since the upper hip accommodates to the movement of the upper body, it is an excellent buttress for constant transfer of weight from the arm to the supporter of the invention, during ambulatory and stationary activities by the patient. This allows the patient to transfer the weight of the supported limb to the patient's side or front while walking, thereby making transit through doorways, into elevators, and within crowded areas, much easier to maneuver.

The base may have a design that tends to conform to the shape of the body member that it is most likely to be used with as the support surface and this makes the function of the base, hence the whole support, more accommodating to the patient because more of the base surface contacts the supporting body surface. In the usual case, the edge shape of the base will preferably be arcuate following the general arcuate shape of the body portion most likely to be used.

The other end of the limb supporter of the invention is the limb support means. It has been determined that a stable limb supporter that allows mobility, should also provide a stable surface means for holding the limb in question. Moreover, a stable limb supporter that is used to support an arm or a leg should possess a design that suits the support of both limbs. It has been determined that the limb support means that directly holds the limb should be strong enough to support the weight of the limb, have dimensions suitable for engaging the limb and holding it in a stable position, and have dimensions relative to the base's dimensions, that allows stable control over the position of the limb during peripatetic use with or without the use of harnesses or straps (or other similar devices which a patient might find difficult to use) to hold the limb in place. The limb supporter of the invention employs as the limb support means, a semicircular-like and trough-like platform configured to have diameter at least as large as the diameter of the widest portion of the limb to be supported and a length sufficient to resist tilting of the limb supporter during ambulatory and stationary use. In the typical case, the length of the limb support means is at least one-quarter ($\frac{1}{4}$) the length of the patient's forearm, usually at least 4 inches in length and preferably, at least 5 inches in length. This kind of platform supplies solid surface acts like a cradle to provide support across enough of the limb's surface so as to support the limb while the body undergoes movement and acts to resist potential movement of the limb. By having the limb arcuately and longitudinally supported, any transfer of the weight of the limb on the limb support means will be uniformly transferred to the base, and the weight shift will be resisted, thereby holding the limb in a fixed position.

This relatively stable and substantially fixed positioning of the limb supporter on the user's body is accomplished without the need for any extraneous positioning or holding means such as a pulley arrangement. It is elegantly, effectively and simply accomplished by the frictional-engagement cushioning layer at the base of the supporter while the arm is being comfortably and stably cradled by the limb support means. The limb supporter is quickly and conveniently repositioned on the body by simply lifting the arm that is being supported thereon and moving it to another position or shifting the supporter to another position with the free hand (or with the assistance of another person) along the hip and allowing the supported limb to follow the repositioning of the supporter while held in place and fully supported by the limb supporter of the invention.

Thus, the present invention relates to a portable limb support device adapted to provide multi-positional support for a patient using the same, which comprises:
(a) a base having a top and a bottom surface, where the bottom surface has a frictional surface suitable for providing frictional engagement with the patient's body and provides cushioning so that the base can be comfortably rested on a portion of the patient's anatomy;
(b) at least two support members having upper and lower ends, respectively, said lower ends pivotably mounted to said base, each support member having height adjustment means to independently adjust the height of each member relative to the base; and
(c) a limb support means mounted on the upper ends of the at least two support members, said mounting comprising a means to enable the limb support means to be rotatable along its own longitudinal axis.

The present invention provides a limb supporter device which is of simple and practical construction, which is efficient and dependable in use, neat and attractive in appearance, relatively inexpensive, and most importantly, enables an ambulatory patient to utilize such device for the support of an arm in essentially any desired position even when such patient is in a stationary mode transitory to the ambulatory mode.

DETAILED DESCRIPTION OF THE INVENTION

Figures 1, 9:
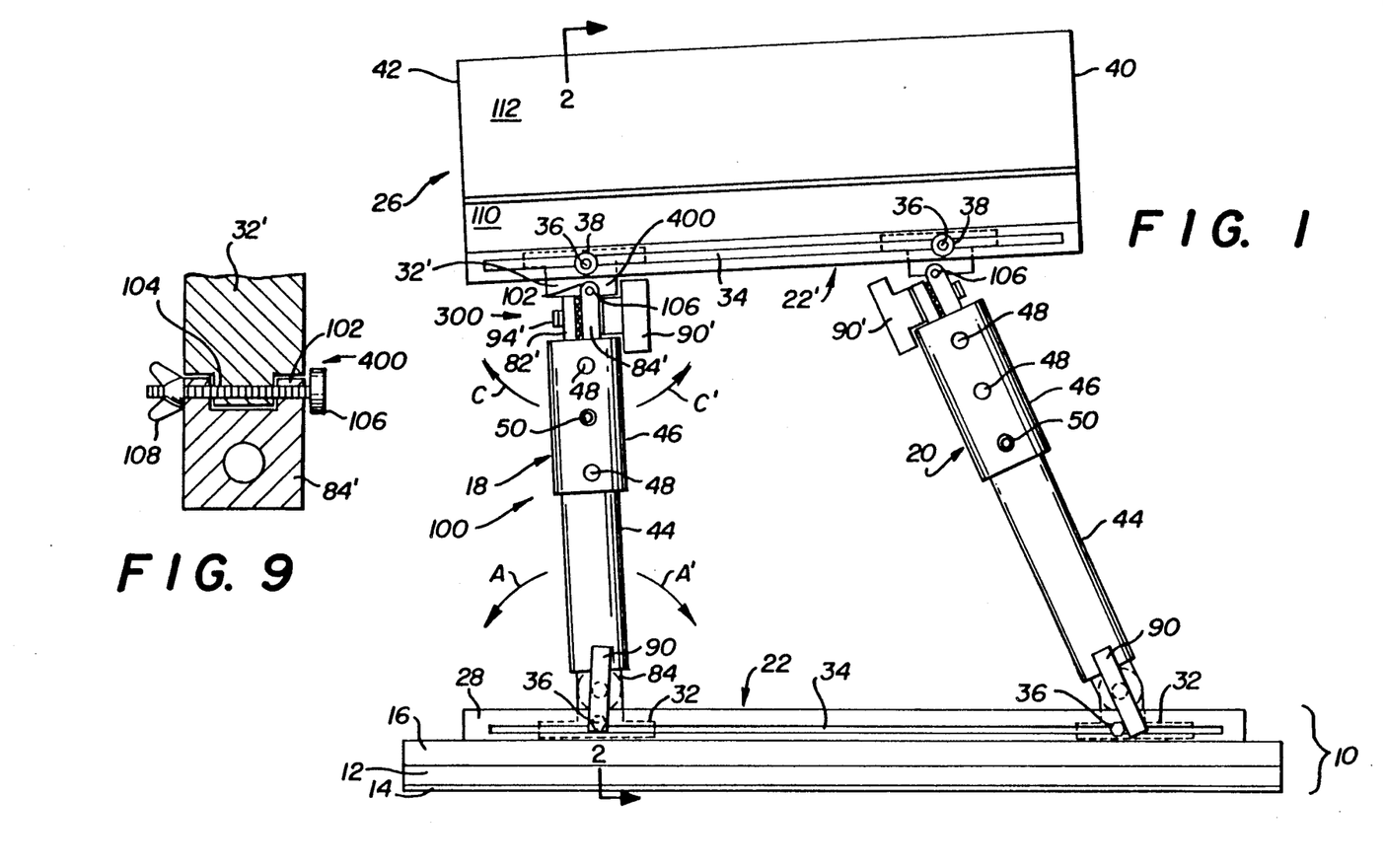
FIG. 1 is a cross-sectional front view of one embodiment of a limb supporter made in accordance with the present invention.
FIG. 9 is a detailed cross-sectional view of one member of a pivoting means taken along line 2—2 of FIG. 1.
Figure 2:
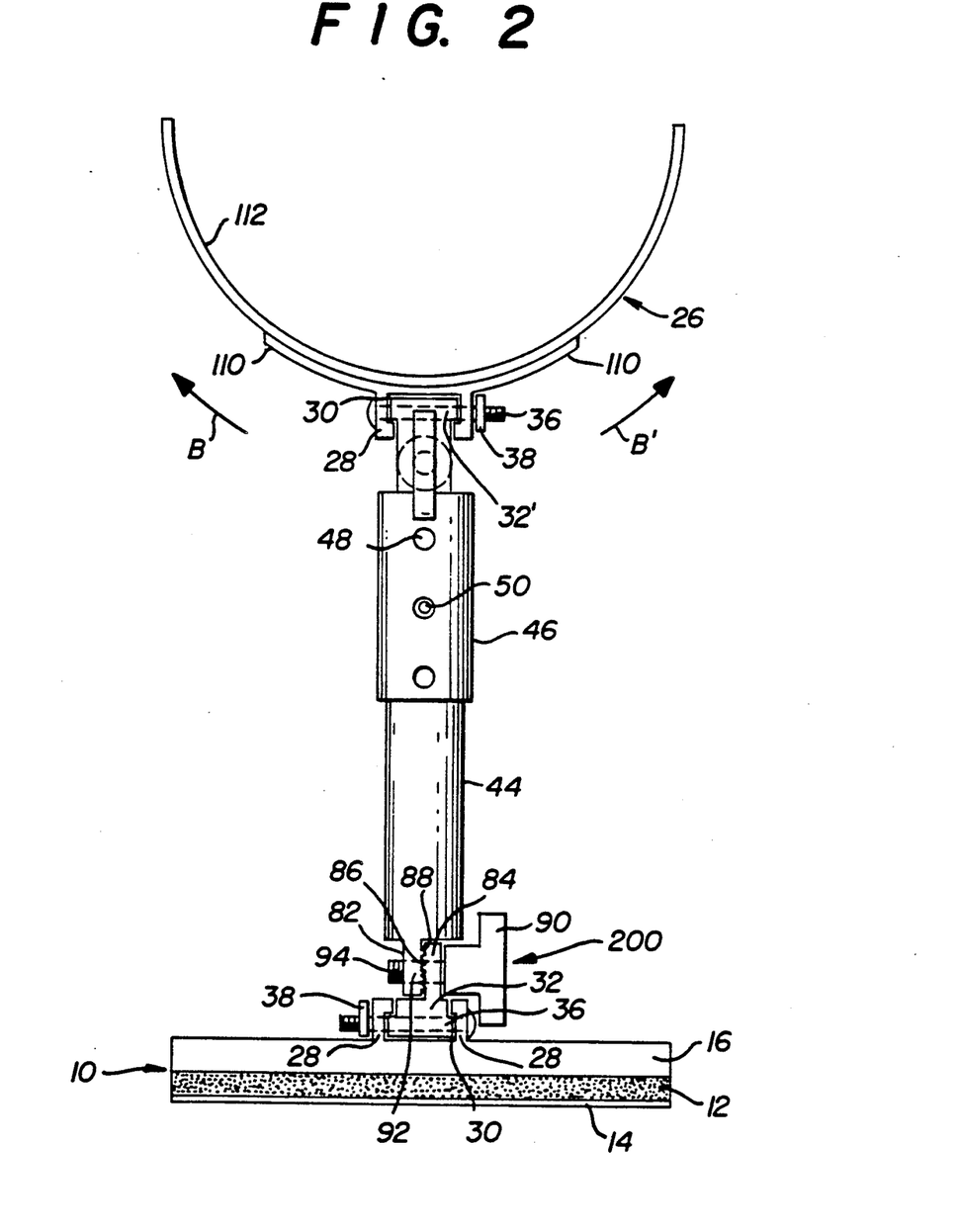
FIG. 2 is a cross-sectional side view of the embodiment shown in FIG. 1 taken along line 2—2.

Referring to FIGS. 1 and 2, in which the same numerals are used to refer to similar elements throughout the drawings, the limb supporter, generally shown as 100, has a base 10. In the embodiment shown in FIG. 1, base 10 is provided with a resilient layer 12 which is positioned on the lowermost bottom surface of the base and upon which the entire limb supporter rests. Resilient layer 12 provides a cushioning layer against the body and provides relatively gentle absorption of the limb's weight by that portion of the body. This avoids the imposition of pain inducing stress by the limb supporter on that portion of the body to which the base is rested. This enables the supporter to be substantially fixed in the placed position on the body with relatively minimum discomfiture to the patient. Associated with resilient layer 12 is frictional layer 14, which comprises the bottom surface of the supporter. Frictional layer 14 is comprised of a material which is suitable for providing effective frictional engagement with the body of the user when utilized in a manner more fully described hereinbelow.

The combination of resilient layer 12 and frictional layer 14 is typically a laminate comprising a soft resilient inner layer 12 bonded to a frictional outer layer 14 of a material that preferably possesses a low enough modulus of elasticity and/or possesses a sufficiently textured surface that the material grips to fabric and/or skin. The textured surface of layer 14 can be imparted by molding a film on a mold containing a mold surface in which the texturing is imparted. Molding can be effected by cast or injection molding processes. The frictional layer may be made of natural or synthetic rubber, polyethylene, polypropylene, polyester, polycarbonate, polyvinylchloride plastisol, and the like, thermoplastic materials. It may be bonded to the resilient layer by an adhesive. The frictional layer 14 may be made of the same material as the resilient layer 12. For example, layer 12 can be made of a polyurethane foam that is provided with a thick skin portion that provides the basis for frictional layer 14. For example, a thin layer of polyurethane foam can be formed as a sheet on a mold possessing a textured surface. As the foam rises on the mold sheet, a denser layer is formed on the mold surface and the denser layer replicates the texture design on the mold surface. In such a case, layers 12 and 14 are made from the same material but there is a sufficient gradient in density of the molded foam so as to create distinct layer portions, designated 12 and 14 herein.

The soft and resilient inner layer 12 includes a wide range of materials, including, but are not limited to, flexible and resilient foamed plastic or rubber compositions which are well known to those skilled in such art, such as latex foamed, flexible polyurethane foam, polyvinylchloride foam, and the like. Also applicable is essentially any material of construction, preferably lightweight, such as an unfoamed plastic, metal, wood, leather, fabric, etc.

The thickness of resilient layer 12 is also not narrowly critical to the invention. It may be made as thin or as thick as desired based on economics, attractiveness and functional purposes. Preferably, the thickness for the particular material utilized for such layer is thick enough to provide the desired degree of cushioning of the base support when the device is rested on a portion of the human anatomy. In the typical case, the resilient layer has a thickness of at least ¼ inch, preferably at least ½ inch, and most preferably, at least ¾ inch. A most suitable resilient layer may be about 1 to about 1½ inches thick.

The frictional layer is attached to base member 16 by any conventional means such as by the use of suitable adhesives, fastening devices, and the like. While the embodiment shown in FIGS. 1 and 2 depict the frictional layer as being present only on the lowermost surface of base member 16, it is to be understood that the present invention is not limited to such a construction. For example, the frictional layer may be positioned on base member 16 such that in addition to being present on its lowermost surface, it also extends above such surface along the vertical walls of base member 16. In fact, in a preferred embodiment of the invention, the frictional layer 14 wraps around the sidewalls of resilient layer 12 and over the exterior sidewalls of member 16 so as to assure frictional engagement even when the limb supported is tilted off the base surface represented by layer 14 so that only an edge portion of layer 14 is engaged on the body or other surface, assisting in the support of the limb.

Figure 3:
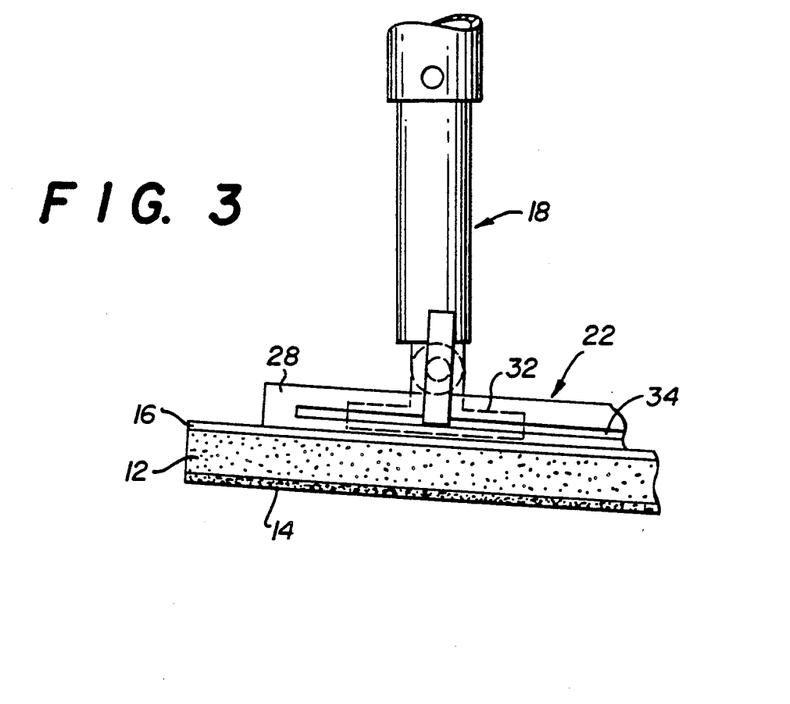
FIG. 3 shows a portion of the cross-section of FIG. 1 with an alternative embodiment for the base limb supporter.

As shown in FIG. 3 which sets forth just a portion of the limb supporter in another embodiment, the combination of the resilient layer 12 and the frictional layer 14 may be much thicker than body member 16. In this preferred embodiment, the resilient layer is comprised of a foamed plastic, such as foamed polyurethane or a foamed latex rubber, covered by a denser frictional plastic or rubber layer 14. This not only provides resilient layer 12 with the desired frictional surface 14 but due to the larger thickness of layer 12 also advantageously provides enhanced resiliency to the limb supporter making it more comfortable in use.

Figure 4:
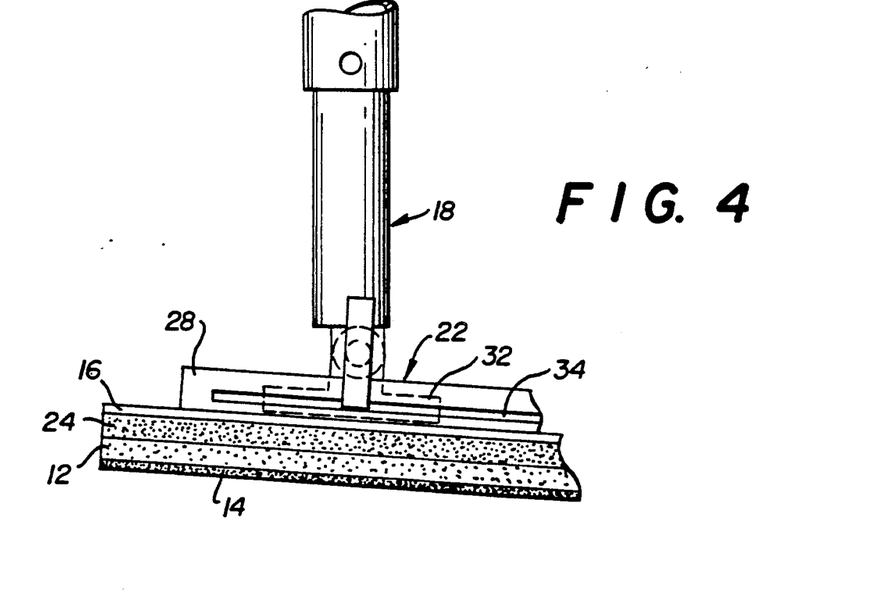
FIG. 4 also shows a portion of the cross-section of FIG. 1 with yet another alternative embodiment for the base of the limb supporter.

Of course, a resilient layer need not be an integral part of the frictional layer. Thus, as shown in FIG. 4, a different resilient layer 24 may be provided above resilient layer 12, preferably interposed between base member 16 and layer 12. Here, the different resilient layer may be comprised of, e.g., a denser latex rubber foam which is adhesively bonded to the less dense resilient layer 12, which in turn possesses an outer surface 14 made of, for example, a vinyl plastisol or a urethane film which serves as the frictional layer 14.

In the embodiment shown in FIGS. 1 and 2, base member 16 is a unitary, integral part of the means by which support members 18 and 20 are respectively mounted to base 10. Thus, a track assembly, generally shown in FIGS. 1 and 2 as 22, is utilized in this embodiment to provide slidable engagement means for the support members. However, it is to be understood that it is not necessary that the means for mounting the support members to base 10 be an integral and unitary part of base member 16. The mounting means for support members 18 and 20 may comprise individual elements which are separately attached to base member 16 (not shown) by any conventional means. Base member 16, whether or not of unitary construction with the mounting means for the support members, can be made of any suitable material which provides structural integrity to the base, if it is already not provided by resilient layer 12. Accordingly, base member 16 may be made from a metal, desirably lightweight such as aluminum, unfoamed plastic, a structural foam plastic, wood, and the like.

In the present invention, it is desirable, although not necessary, to provide support members 18 and 20 with the ability to slide along the longitudinal axis of base 10. This better enables the limb support means, generally shown as 26, to be more easily angularly positioned with respect to base 10. In the embodiment of FIGS. 1 and 2, base 10 advantageously contains a slidable engagement means, here track assembly 22, for providing such longitudinal movement to the support members. It is not necessary, however, that each support member be provided with such slidable engagement means.

A slidable engagement means, namely a track assembly 22', may also desirably be provided in the limb support means as well, as shown in FIGS. 1 and 2. It is understood that such a slidable engagement means in the limb engaging member is only preferred and not required.

In the embodiment shown in FIGS. 1 and 2, the slidable engagement means is a track assembly 22 (or track assembly 22') comprised of a channel forming a track 30 which is made by vertical elements 28 and a track engagement member 32 which is pivotably mounted to the lower ends of the support members with respect to track assembly 22 (and the upper ends of the support members with respect to track assembly 22'). As shown, track 30 may extend substantially along the entire length of base 10. In order to secure track engagement member 32 in a fixed position relative to track 30, the track is provided with a suitable locking means. In the embodiment shown in the Figures, a longitudinal slit 34 is provided in each of vertical elements 28 and a bore is provided in each of the slidable track engagement members 32 so as to accommodate a bolt 36 which is tightened with a threaded knob 38. It is to be understood that slidable engagement means other than a track assembly such as that described above which are well known to those skilled in the art may also be utilized in the present invention. So too, a locking means other than longitudinal slit 34, threaded bolt 36 and threaded knob 38 may also be suitable.

While only support members 18 and 20 are shown in FIGS. 1 and 2, it is understood that even 3 or more of such support members may be used if so desired. Generally, the use of only two support members is entirely sufficient. The support members are provided with means such that their respective heights are independently adjustable thereby enabling limb support means 26 to be angularly positioned with respect to base 10 so as to better accommodate a user's limb in different applications. Thus, with support member 18 at one adjusted height and support member 20 at an extended height which is greater than the height of support member 18 as shown in FIG. 1, the right side 40 of limb engaging member 26 is correspondingly higher than its left side 42 resulting in the limb engaging member being angularly disposed with respect to base 10. Adjustments to this angle may also be made by keeping the height of the support members constant while sliding the ends of the support members with either or both of the slidable engagement means situated in the base or in the limb support means. Alternatively, a combination of these adjustments may be made to provide the desired support and angle.

The support members may comprise any conventional mode of construction which enables them to be independently adjusted in height. The specific mode is not narrowly critical to the present invention.

Thus, in FIGS. 1 and 2, the support members are comprised of telescopically engaged elements. The upper end of lower telescoping element 44 is concentrically disposed within upper telescoping element 46. While only two telescoping elements are depicted in the drawings in association with each support member, it is understood that if desired, 3 or more such elements may also be utilized. So too, the telescoping elements need not be circular in cross-section as shown in the drawings but may possess any cross-sectional profile, such as rectangular, elliptical, triangular, and the like.

In the embodiment shown in FIGS. 1 and 2, the upper telescoping element 46 is provided with openings 48 through which a pin 50, attached to lower telescoping element 44, is introduced in order to secure the two telescoping elements in a fixed height position. This securement means is better shown in FIG. 5. Pin 50 is attached to a biased element 54 which is attached to the lower telescoping element 44 at 52 by welding, riveting or other equally suitable means. The rigidity of element 54 tends to oppose an inward force upon pin 50 such that the pin desirably stays biasly positioned through one of openings 48. When it is desired to adjust the height of the support member, pin 50 is pushed inwardly while the height adjustment is made to align the pin with one of the other openings 48. When the pin is released, it moves outwardly through the opening and securely holds the telescoping elements in place at the new height position.

Figure 5:
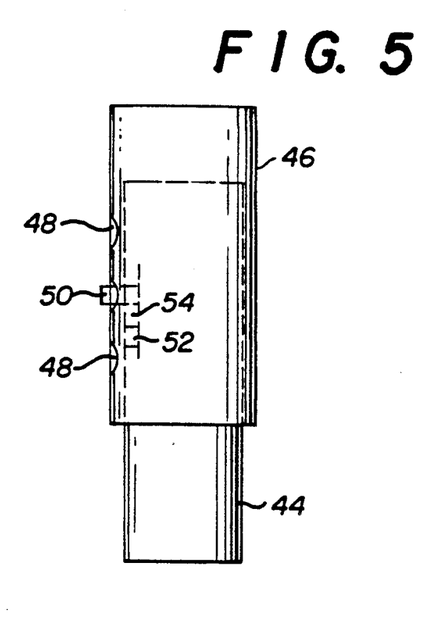
FIG. 5 is a cross-sectional side view of one embodiment of the present invention showing a support member and the means by which the telescoping elements of the support member interconnect.
Figure 6A:
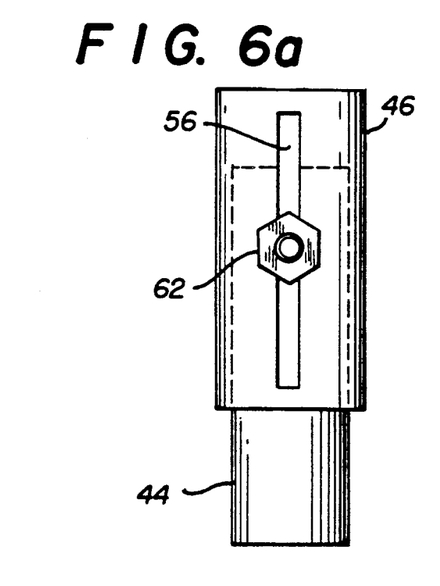
FIGS. 6a and 6b show cross-sectional views of another embodiment of the present invention showing yet another means by which the telescoping elements of the support member interconnect.
Figure 6B:
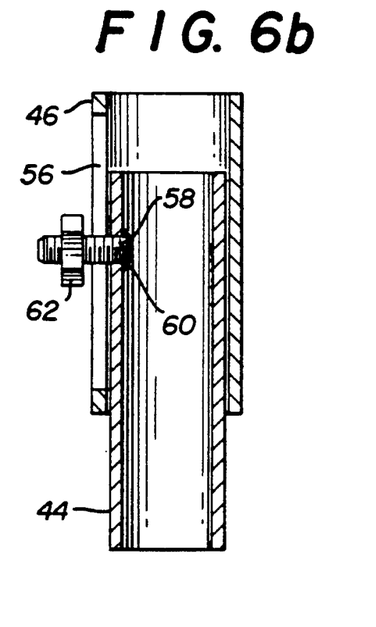

Of course, the present invention is not limited to the embodiment shown in FIG. 5. Instead, as shown in FIGS. 6 and 6b, other means for securing the telescoping elements of the support members may also be used. Accordingly in FIG. 6, a slit 56 is provided in upper telescoping member 46. A bolt 58 is permanently affixed by welding or otherwise to lower telescoping member 44 at point 60. Bolt 58 passes outwardly from the lower telescoping member, through the slit 56, and is secured in place, along with the lower telescoping element to which it is rigidly attached, with threaded knob 62. The use of a slit to traverse the height of the telescoping element is advantageous inasmuch as it allows a universal adjustment in the height of the support member. In contrast, the use of openings 48 with pin 54 in FIG. 5 is limited to the number of openings 48 that are provided in the telescoping element. Other means for securing the telescoping elements of the support member which are well known to those skilled in the art may also be utilized in the present invention.

Figure 7A:
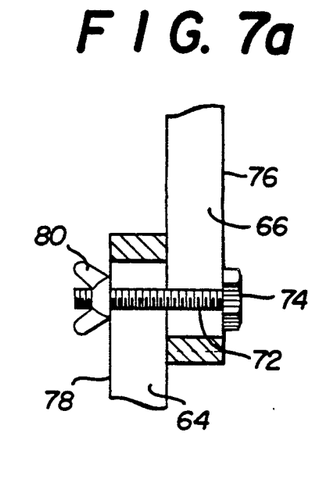
FIGS. 7a and 7b show cross-sectional views of another embodiment of the present invention showing a support member comprised of slidably engaged juxtaposed elements secured to one another with a mutually cooperating bolt and wing nut.
Figure 7B:
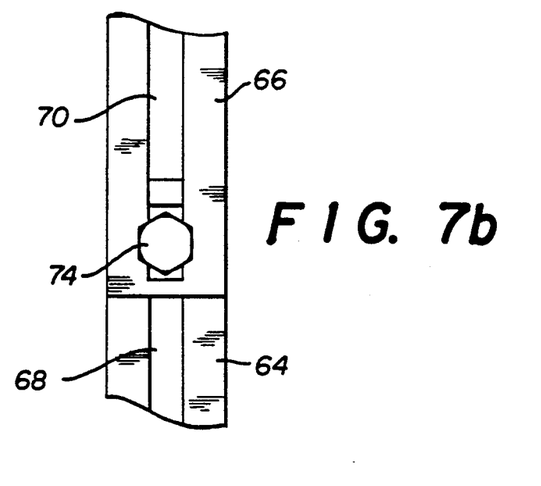

Another mode of construction for the support members is shown in FIGS. 7a and 7b. Here, a support member is comprised of a lower element 64 having a longitudinal slit 68 which is slidably engaged and juxtaposed with an upper element 66 having a longitudinal slit 70 which is mutually aligned with slit 68. A bolt 72 having a head 74 resting on the outermost surface 76 of upper element 66 respectively passes through slit 70 of upper element 66 and then through slit 68 of lower element 64 and emerges at outermost surface 78 where it is secured by wing nut 80. This type of construction for the support members also offers universal height adjustment. Again, the means for securing element 64 and 68 so that a height adjustment is fixed in place need not be limited to the use of bolt 72 and wing nut 80. While such securing means is easy to use and relatively inexpensive to manufacture and incorporate into the limb supporter of the present invention, any other conventional securing means may also be utilized.

Desirably, each end of the support member is pivotably mounted to base 10 and limb support means 26, respectively. Pivoting of both the lower and upper ends of the support members enables them to pivotably move as they are being slid along track assembly 22 and 22', respectively. Most importantly, however, yet an additional pivoting means is provided for the upper ends of the support members which enables the limb support means to be rotatable about its own longitudinal axis.

It is to be noted that while the Figures show support members 18 and 20 being pivotably mounted at the top surface of base 10 or the lowermost surface of the limb support means 26, it is not necessary that this be the location of where the support members are mounted. By means not shown, the support members may, if desired, by pivotably mounted at the sides of base 10 and/or limb support means 26.

The means for pivotably mounting the support member is not narrowly critical to the present invention. Essentially any means for providing such pivotable mounting can be utilized as long as it can readily and easily be adjusted to accommodate the needs of the user.

One such pivotable mounting means is shown generally as 200 in FIGS. 1 and 2. There, referring to FIG. 2 and the lower end of the support member, eye 82 having teeth 86 of lower telescoping element 44 mutually cooperates with eye 84 having teeth 88 of track engagement member 32. Eye 82 is provided with a threaded bore 92 which engages with the threads of bolt 94 having a T-shaped knob 90. The turning of T-shaped knob 90 in a counterclockwise direction allows teeth 86 and 88 to sufficiently separate so that they are no longer engaged. The support member 18 is then free to be pivoted in the direction shown by arrows A—A' in FIG. 1, e.g., about the axis formed by bolt 94, as the support member is slid along track assembly 22. When T-shaped knob 90 is turned in a clockwise direction, teeth 86 and 88 are once again engaged and the support member is locked in position.

A similar pivoting means is provided at the upper ends of the support members as well, generally shown as 300 in FIGS. 1 and 2, and is designated with prime numbers, e.g., bolt 94'. Pivoting means 300 also utilizes an eye 82' of the upper end of support member 18 and an eye 84' of track engagement member 32', as well as essentially all of the remaining elements as hereinabove discussed with respect to pivoting means 200 for the lower end of support member 18. However, pivoting means 300 is provided in the limb supporter of the present invention not for the purpose of providing further mobility to the support member, but rather to provide freedom of movement for the limb support means. Accordingly, the entire pivoting means 300 is positioned such that it is rotated 90 degrees relative to the position of pivoting means 200. By doing so, when T-shaped knob 90' of pivoting means 300 is loosened, the entire limb support means is then free to rotate in the directions shown by arrows B—B' in FIG. 2. This facilitates the user of the limb supporter to rotate the limb support means to any desired position, particularly after the limb supporter has been placed up against the user's body for support and it is generally desirable for the open end of the limb support means to be in an upwardly facing direction.

The particular pivoting means embodiment discussed in FIGS. 1 and 2 is only illustrative. The present invention is not limited to the use of such a pivoting means. Any conventional pivoting means may be used provided that it is capable of enabling the support members and/or the limb support means to be pivoted in the manner described above. Thus, a pivoting means such as the one shown in FIG. 8 may also be utilized.

Figure 8:
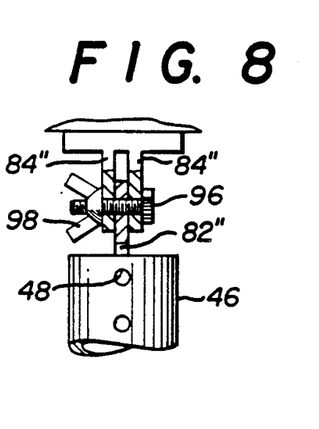
FIG. 8 is a cross-sectional diagram of a close-up of a pivoting means embodiment which may be used in the present invention.

FIG. 8 is a close-up of the upper telescoping end 46 of a support member having an eye 82''. Track engaging member 32' provides eyes 84''. A threaded bolt 96 is passed through each of the respective eyes and is tightened by wing nut 98 so as to secure the limb support means in place.

In order to provide a means such that the support member itself can be pivoted at its upper end, where it connects to the limb support means, an additional pivoting means 400 may be provided as generally shown in FIG. 9 and at the upper end of support member 18. This additional pivoting means helps facilitate the movement of the support member along the track assembly 22' in limb support means 26.

FIG. 9 shows a cross-sectional detailed view of only track engaging member 32' of track assembly 22'. In contrast to pivoting means 200 in which eye 84 of track engaging member 32 is a unitary, integral part of the track engaging member, eye 84' in pivoting means 300 is a separate element from the rest of track engaging member 32'. Eye 84' contains additional eyes 102 which mutually cooperate with eye 104 of track engaging member 32' such that a bolt 106 can be passed through eyes 102 and 104, respectively, and be tightened with, for example, a wing nut 108. The loosening and tightening of wing nut 108 now enables support member 18 to pivot at its upper end in the directions shown by arrows C—C'.

In the embodiment shown in FIGS. 1 and 2, limb support means 26 is comprised of track assembly 22' which has elongated arms 110 and arcuate member 112. Arms 110 from track assembly 22' are fixedly attached to arcuate member 112 in any conventional manner. In an alternative embodiment, the entire limb support means may be comprised of one integral, unitary member.

The limb support means should be made of material which can substantially maintain its structural integrity so as to provide the necessary support of a limb while still desirably being lightweight. Suitable materials include, but are not limited to, lightweight metals such as aluminum, rigid plastics, and the like. Preferably, the concave portion of arcuate member 112 is cushioned or lined (not shown) with appropriate soft materials so as to provide more comfort to the user.

In an alternative embodiment (not shown), arcuate member 112 may be made as a wire frame, for example, from a suitable rigid material such that a fabric or leather type material may be placed about said frame.

In use, the limb supporter of the present invention is able to provide the user with an endless variety of positions for supporting an arm or a leg. The multi-positional limb supporter can be placed on any fixed support such as a table, chair, bed, and the like and positioned such that the height and angle of the limb support means is at a desirable height and angle to facilitate an inclined position of the limb in order to allow for a natural, gravity-encouraged, flow of fluids throughout the limb to prevent or decrease the accumulation of fluids. Because of the adjustability of the base relative to the limb arcuate.

Figure 10A:
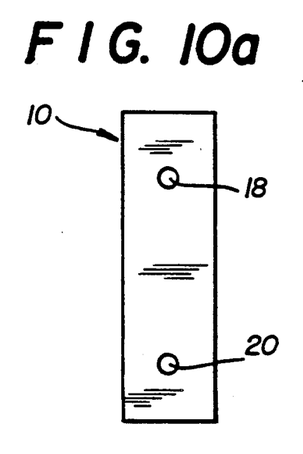
FIGS. 10a, 10b and 10c are plan views of different base member shapes for the limb support device of the invention.
Figure 10B:
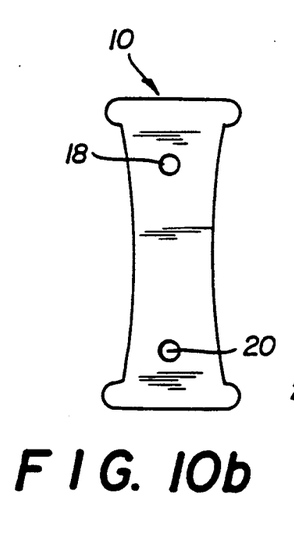

In its most advantageous application, the limb supporter of the present invention is capable of being utilized for supporting an arm even when the user is stationary or ambulatory. As shown in FIGS. 10a and 10b, the limb supporter may simply be placed on the hip of the user and the arm placed in the limb support means thereby supporting the limb and avoiding gravitational stress on proximal joints, e.g., at the shoulder. The device of the invention is employable with the need for constant adjustment, and if adjustment is required for comfort and more effective utility, then the device is easily and readily adjusted to suit the comforts of the patient. In the usual case, there will be an initial adjustment of the limb support device to suit the needs of the patient, and thereafter, the supporter will be used without further adjustments having been made. However, by adjusting the various pivoting means, adjusting the heights of the support members, positioning the support members along the track assemblies, and rotating the limb support means to an upwardly facing position (all of which can be done by the turn of a few wing nuts or knobs), the entire limb supporter can quickly and easily be positioned such that the arm is in a proper inclined position relative to the body and ground. The limb supporter, due to the frictional layer and the weight of the arm, will stay substantially in place even while the user moves about.

Arcuate member 112 is semicircular-like in shape wherein to form a trough into which a limb can be positioned. Semicircular-like means a curved shape that generally follows the shape of a circle when viewed cross-sectionally of the longitudinal direction of member 112. The curved shape may be parabolic or round, provided the diameter of the curved shape is large enough to comfortably receive the girth of the limb. Moreover, the longitudinal length of member 112 is sufficient to provided enhanced stability on movement of the device. The arcuate member may be sized according to the size of the patient, such as large, medium and small sized arcuate members to serve patients of corresponding limb sizes.

Though the arcuate member 112 is shown without the use of straps, and such is the preferred practice of the invention, straps can be incorporated into the arcuate member so as to further hold the limb in the member. This feature has obvious advantages and disadvantages. A better design for the arcuate member 112 is to form the sidewalls of the member such that they are fairly high and form a slight reentry angle into the limb placed within the member. This serves to use the sidewalls as clamps making the limb more secure within the arcuate member 112.

Figure 10C:
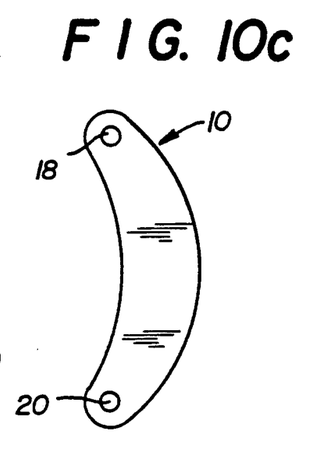

FIGS. 10a, 10b and 10c illustrate some plan views of a number of the shapes that the base 10 of the device of the invention may take. The rectangular design of FIG. 10a is most conventional and would be the typical shape the base will take. The concave side base of FIG. 10b provides contouring for use of the hip as the base for the device. FIG. 10c utilizes a single contoured side which eliminates extraneous corners making the device more maneuverable by the patient.

Figure 11:
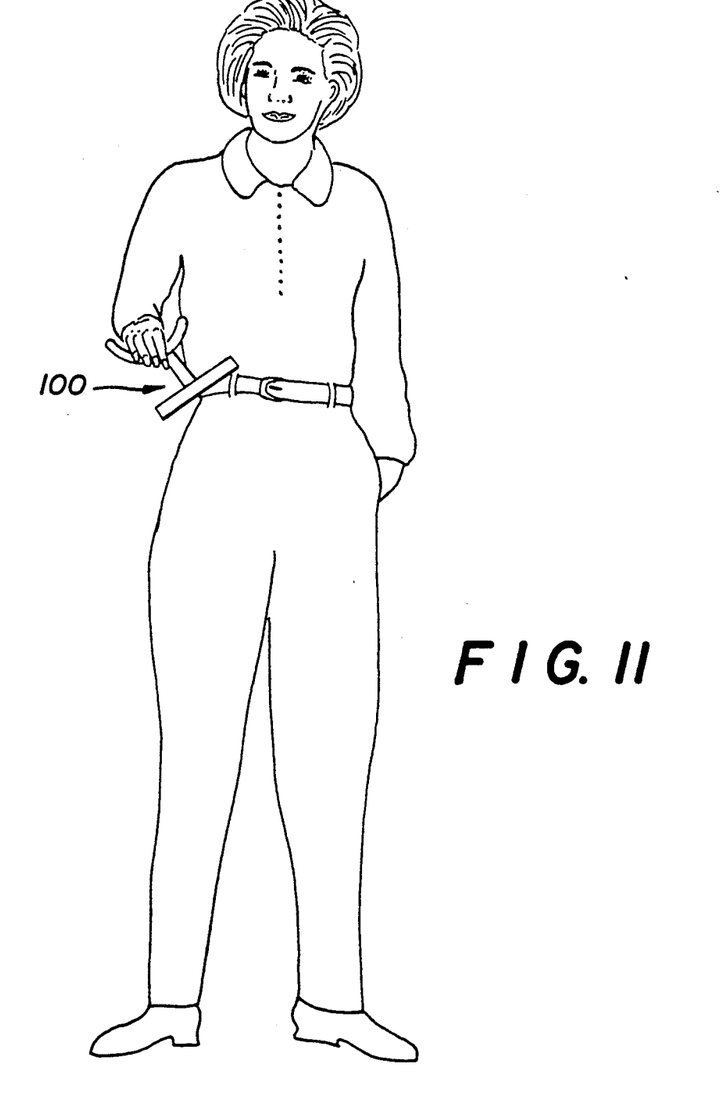
FIG. 11 is proportional views of the limb supporter of the present invention as it is being used by a patient needing arm support but who is ambulatory.

FIG. 11 is a front view of a person supporting his/her arm on the device 100 of the invention where the base is rested on the hip. Device 100 is easily manipulated so that the base is repositioned to the abdominal region while at the same time supporting the arm.

I claim:

1. A portable limb support device adapted to provide multi-positional support for a patient using the same, which comprises:
   (a) a base having a top and a bottom surface, where the bottom surface has a frictional surface suitable for providing frictional engagement with the patient's body and provides cushioning so that the base can be comfortably rested on a portion of the patient's anatomy;
   (b) at least two support members having upper and lower ends, respectively, said lower ends pivotably mounted to said base, each support member having height adjustment means to independently adjust the height of each member relative to the base; and
   (c) a limb support means mounted on the upper ends of the at least two support members, said mounting comprising a means to enable the limb support means to be rotatable along its own longitudinal axis.

2. The limb support device of claim 1, wherein the support members are mounted to the top surface of the base.

3. The limb support device of claim 1, wherein the mounting of the support members to the base additionally contains a means to enable the support members to be slidably engaged with the base.

4. The limb support device of claim 1, wherein the mounting of the support members to the limb support means also contains a means to enable at least one of the supporting members to be slidably engaged with the limb support means.

5. The limb support device of claim 3, wherein the slidable engagement means comprises a track and a sliding track member cooperatively engaged with said track.

6. The limb support device of claim 4, wherein the slidable engagement means comprises a track and a sliding track member cooperatively engaged with said track.

7. The limb support device of claim 5, wherein the base is provided with said track and at least one support member is provided with said sliding track member positioned on its lower end.

8. The limb support device of claim 6, wherein the base is provided with said track and at least one support member is provided with said sliding track member positioned on its lower end.

9. The limb support device of claim 5, where the limb support means is provided with said track and the at least one support member is provided with said sliding track member positioned on its upper end.

10. The limb support device of claim 6, where the limb support means is provided with said track and the at least one support member is provided with said sliding track member positioned on its upper end.

11. The limb support device of claim 1, wherein the frictional layer is comprised of a foamed plastic or rubber composition.

12. The limb support device of claim 1, wherein the base contains a resilient layer above the frictional layer.

13. The limb support device of claim 1, wherein the resilient layer is also the frictional layer.

14. The limb support device of claim 1, wherein a support member is comprised of telescopically engaged elements which define the height adjustment means.

15. The limb support device of claim 1, wherein a support member is comprised of slidably engaged, juxtaposed elements which define the height adjustment means.

* * * * *